US012358946B2

(12) United States Patent
Meh et al.

(10) Patent No.: US 12,358,946 B2
(45) Date of Patent: Jul. 15, 2025

(54) METHOD FOR PURIFYING ANTIBODIES

(71) Applicants: United Therapeutics Corporation, Silver Spring, MD (US); The United States of America as Represented by the Secretary, Department of Health and Human Services, Bethesda, MD (US)

(72) Inventors: David Meh, Columbia, MD (US); Timothy Atolagbe, Elkridge, MD (US); G. Mark Farquharson, Vienna, VA (US); Samir Shaban, Frederick, MD (US); Mary Koleck, Rockville, MD (US); George Mitra, Potomac, MD (US)

(73) Assignees: United Therapeutics Corporation, Silver Spring, MD (US); The United State of America, as Represented by the Secretary, Department of Health and Human Services, Bethesda, MD (US)

( * ) Notice: Subject to any disclaimer, the term of this patent is extended or adjusted under 35 U.S.C. 154(b) by 1112 days.

(21) Appl. No.: 17/154,678

(22) Filed: Jan. 21, 2021

(65) Prior Publication Data

US 2021/0139535 A1     May 13, 2021

Related U.S. Application Data

(63) Continuation of application No. 14/995,278, filed on Jan. 14, 2016, now Pat. No. 10,906,935, which is a continuation of application No. PCT/US2015/042241, filed on Jul. 27, 2015.

(60) Provisional application No. 62/028,994, filed on Jul. 25, 2014.

(51) Int. Cl.
| | |
|---|---|
| *C07K 1/36* | (2006.01) |
| *B01D 15/12* | (2006.01) |
| *B01D 15/18* | (2006.01) |
| *B01D 15/24* | (2006.01) |
| *B01D 15/36* | (2006.01) |
| *B01D 15/38* | (2006.01) |
| *B01D 61/16* | (2006.01) |
| *C07K 1/14* | (2006.01) |
| *C07K 1/18* | (2006.01) |
| *C07K 1/34* | (2006.01) |
| *C07K 16/18* | (2006.01) |
| *C07K 16/30* | (2006.01) |

(52) U.S. Cl.
CPC .............. *C07K 1/36* (2013.01); *B01D 15/125* (2013.01); *B01D 15/1871* (2013.01); *B01D 15/24* (2013.01); *B01D 15/362* (2013.01); *B01D 15/363* (2013.01); *B01D 15/3809* (2013.01); *B01D 61/16* (2013.01); *C07K 1/14* (2013.01); *C07K 1/18* (2013.01); *C07K 1/34* (2013.01); *C07K 16/18* (2013.01); *C07K 16/3084* (2013.01); *B01D 2315/16* (2013.01); *C07K 2317/14* (2013.01); *C07K 2317/24* (2013.01); *C07K 2317/73* (2013.01); *C07K 2317/76* (2013.01)

(58) Field of Classification Search
CPC ... C07K 1/36; C07K 1/14; C07K 1/18; C07K 1/34; C07K 16/18; B01D 15/125; B01D 15/1871; B01D 15/24; B01D 15/362; B01D 15/363; B01D 15/3809; B01D 61/16; B01D 2315/16; B01D 61/146
See application file for complete search history.

(56) References Cited

U.S. PATENT DOCUMENTS

| | | | |
|---|---|---|---|
| 4,436,626 | A | 3/1984 | Schnabel |
| 4,728,430 | A | 3/1988 | Dileo et al. |
| 4,883,865 | A | 11/1989 | Kubek |
| 5,225,194 | A | 7/1993 | Suer |
| 5,695,760 | A | 12/1997 | Faanes et al. |
| 6,218,513 | B1 | 4/2001 | Anthony-Cahill et al. |
| 6,406,631 | B1 | 6/2002 | Collins et al. |
| 6,423,231 | B1 | 7/2002 | Collins et al. |
| 6,689,871 | B1 | 2/2004 | Wolfe et al. |
| 9,139,632 | B2 | 9/2015 | Bobrowicz et al. |
| 10,329,323 | B2 * | 6/2019 | Shaban .............. C07K 16/3084 |

(Continued)

FOREIGN PATENT DOCUMENTS

| | | |
|---|---|---|
| JP | 2008-546387 A | 12/2008 |
| JP | 2009-539403 A | 11/2009 |

(Continued)

OTHER PUBLICATIONS

Fahrner, RL et. al. "Industrial Purification of Pharmaceutical Antibodies: Development, Operation, and Validation of Chromatography Processes", 2001, Biotechnology and Genetic Engineering Reviews, 18(1), 301-327. (Year: 2001).*

(Continued)

*Primary Examiner* — Nelson B Moseley, II
*Assistant Examiner* — Alyssa Rae Stonebraker
(74) *Attorney, Agent, or Firm* — Foley & Lardner LLP

(57) ABSTRACT

Disclosed here includes a method for purifying a biologic composition, comprising diafiltering the biologic composition into a composition comprising phosphate buffered saline (PBS) to obtain a purified composition. The method disclosed here can be particularly useful for removing one or more impurities from the biologic composition, such as bis(2-hydroxyethyl)amino-tris(hydroxymethyl)methane (Bis-tris).

12 Claims, 5 Drawing Sheets

(56) References Cited

U.S. PATENT DOCUMENTS

| | | | |
|---|---|---|---|
| 10,906,935 B2* | 2/2021 | Meh | C07K 1/18 |
| 2002/0146388 A1 | 10/2002 | Gillies | |
| 2010/0221746 A1 | 9/2010 | Phillips et al. | |
| 2011/0152171 A1 | 6/2011 | Weston-Davies | |
| 2013/0336957 A1 | 12/2013 | Wang et al. | |
| 2014/0193876 A1 | 7/2014 | Goerke et al. | |
| 2014/0323698 A1* | 10/2014 | Duthe | C07K 16/12 |
| | | | 252/364 |
| 2015/0110799 A1 | 4/2015 | Ramasubramanyan et al. | |
| 2018/0136242 A1 | 5/2018 | Lee et al. | |
| 2019/0330269 A1 | 10/2019 | Shaban et al. | |

FOREIGN PATENT DOCUMENTS

| | | | | |
|---|---|---|---|---|
| WO | WO-01/82958 | A2 | 11/2001 | |
| WO | WO-2006/138275 | A2 | 12/2006 | |
| WO | WO-2007/145840 | A2 | 12/2007 | |
| WO | WO-2009/016651 | A1 | 2/2009 | |
| WO | WO-2010/141039 | A1 | 12/2010 | |
| WO | WO-2012/160536 | A1 | 11/2012 | |
| WO | WO-2013/060867 | A2 | 5/2013 | |
| WO | WO-2013075849 | A1 * | 5/2013 | B01D 15/3809 |
| WO | WO-2013/189554 | A1 | 12/2013 | |

OTHER PUBLICATIONS

Wang, W et. al. "Antibody Structure, Instability, and Formulation", 2007 Journal of Pharmaceutical Sciences, 96(1), 1-26. (Year: 2007).*

Ahrer, K et. al. "Effects of ultra-/diafiltration conditions on present aggregates in human immunoglobulin G preparations", 2006, Journal of Membrane Science, 274, 108-115. (Year: 2006).*

Schwartz, L "Diafiltration for Desalting or Buffer Exchange", 2003, BioProcess International, 43-49. (Year: 2003).*

Zeng, Y et. al. "Anti-neuroblastoma effect of ch14.18 antibody produced in CHO cells is mediated by NK-cells in mice", 2005, Molecular Immunology, 42, 1311-1319. (Year: 2005).*

Communication of Notice of Opposition dated Apr. 14, 2021 in EP 15750191.7, 33 pages.

Communication of Notice of Opposition dated Apr. 23, 2021 in EP 15750191.7, 6 pages.

Declaration of Dr. Gary Whale dated Apr. 1, 2021, 5 pages, filed as D4 in Opposition against Ep 3172220B1.

GE Healthcare Life Sciences Multimodal Chromatography Handbook, 2013, 115 pages.

GE Healthcare Life Sciences, CaptoTM adhere instructions 28-9064-05 AC, 2012, 40 pages.

Gillies, Stephen D., "A new platform for constructing antibody-cytokine fusion proteins (immunocytokines) with improved biological properties and adaptable cytokine activity," Protein Engineering, Design & Selection, 2013, 26(10):561-569.

Goswami et al., "Developments and Challenges for mAb-Based Therapeutics," Antibodies, 2013, 2:452-500.

Han et al., "Recovery and Purification of Antibody," Chapter 14 in Antibody Expression and Production, Cell Engineering 7, M. Al-Rubeai, Ed., 2011, 305-340.

Harlow et al., Antibodies: A Laboratory Manual, 1988, p. 287.

Horenstein et al., "Design and scaleup of downstream processing of monoclonal antibodies for cancer therapy: from research to clinical proof of principle," Journal of Immunological Methods, 2003, 275:99-112.

Klimyuk et al., "Production of Recombinant Antigens and Antibodies in Nicotiana benthamiana Using 'Magnifection' Technology: GMP-Compliant Facilities for Small- and Large-Scale Manufacturing," Current Topics in Microbiology and Immunology, 2012, 375:127-154.

Li et al., "Construction and characterization of a humanized anti-human CD3 monoclonal antibody 12F6 with effective immunoregulation functions," Immunology, 2005, 116:487-498.

Liu et al., "Recovery and Purification Process Development for Monoclonal Antibody Production," mAbs, Sep./Oct. 2010, 2(5):480-499.

Parfitt, Kathleen and Martindale, William; Martindale: The Complete Drug Reference, London UK, Pharmaceutical Press, 1999, index.

Rowe et al., Handbook of Pharmaceutical Excipients, 6th Ed., 2009, Pharmaceutical Press, contents.

Scopes, Robert K., Protein Purification: Principles and Practice, 3rd Ed., Springer-Verlag New York, Inc., 1994, 351-352.

Soman et al., "Analytical characterization of ch14.18, A mouse-human chimeric disialoganglioside-specific therapeutic antibody," mAbs, Jan./Feb. 2012, 4(1):84-100.

Van Reis et al., "Bioprocess membrane technology," Journal of Membrane Science, 2007, 297:16-50.

Warne et al., "Development of high concentration protein biopharmaceuticals: The use of platform approaches in formulation development," Eur. J. Pharm & Biopharm., 2011, 78:208-212.

U.S. Appl. No. 16/447,439, filed Jun. 20, 2019, Shaban et al.

EMD Millipore, "A Hands-On Guide to ultrafiltration/diafiltration optimization using Pellicon Casettes," 2013, 1-12.

Fahrner et al,. "Industrial purification of pharmaceutical antibodies: development, operation, and validation of chromatography processes," Biotechnology and Genetic Engineering Reviews, 2001, 18:301-328.

GE Healthcare Life Sciences, Instructions 28-9064-05 CaptoTM adhere Affinity Chromatography product manual, 2012, 40 pages.

Gillies et al., "High-level expression of chimeric antibodies using adapted cDNA variable region cassettes," Journal of Immunological Methods, 1989, 125:191-202.

Gilman et al., "Phase I Study of ch14.18 With Granulocyte-Macrophage Colony-Stimulating Factor and Interleukin-2 in Children With Neuroblastoma After Autologous Bone Marrow Transplantation or Stem-Cell Rescue: A Report From the Children's Oncology Group," Journal of Clinical Oncology, Jan. 1, 2009, 27(1):85-91.

Handgretinger et al., "A Phase I Study of Human/Mouse Chimeric Anti-ganglioside GD2 Antibody ch14.18 in Patients with Neuroblastoma," European Journal of Cancer, 1995, 31A(2):261-267.

Schwartz et al., "Diafiltration for Desalting or Buffer Exchange," BioProcess International, May 2003, 43-49.

Schwartz et al., Pall Life Science, Science and Technical Report, Feb. 2003, Diafiltration: A Fast, Efficient Method for Desalting, or Buffer Exchange of Biological Samples, http://www.pall.com/pdfs/Laboratory/02.0629_Buffer_Exchange_STR.pdf.

Shukla et al., "Downstream processing of monoclonal antibodies—Application of platform approaches," Journal of Chromatography B, 2007, 848:28-39.

Zeng et al., "Anti-neuroblastoma effect of ch14.18 antibody produced in CHO cells is mediated by NK-cells in mice," Molecular Immunology, 2005, 42:1311-1319.

* cited by examiner

METHOD FOR PURIFYING ANTIBODIES

CROSS-REFERENCE TO RELATED APPLICATIONS

This application is a Continuation of U.S. application Ser. No. 14/995,278, filed Jan. 14, 2016, which is a Continuation of PCT/US2015/042241, filed Jul. 27, 2015, which claims the benefit of U.S. Provisional Patent Application No. 62/028,994 filed Jul. 25, 2014, the content of which is incorporated herein by reference in its entirety.

BACKGROUND OF THE INVENTION

Known processes for purifying monoclonal antibodies and other biological materials are often required to remove unwanted impurities, which is particularly important when the biologic is produced for therapeutic uses. One way to remove impurities is through diafiltration. Diafiltration is known in the art and described in, for example, Wayne P. Olson, *Separations Technology: Pharmaceutical and Biotechnology Applications* (Interpharm Press 1995); Munir Cheryan, *Ultrafiltration and Microfiltration Handbook* (2d ed. CRC Press 1998); Stefan Behme, *Manufacturing of Pharmaceutical Proteins* (Wiley-VCH 2009); and Glyn N. Stacey, Medicines from Animal Cell Culture (John Wiley 2007), all of which are incorporated herein by reference in their entireties.

Ch14.18 (also referred to herein as "dinutuximab") is an anti-$GD_2$ monoclonal antibody and has been described in Gillies et al., *Journal of Immunological Methods* 125:191-202 (1989), which is incorporated herein by reference in its entirety. When using the ch14.18 antibody for therapeutic purposes, it is important to remove impurities such as bis(2-hydroxyethyl)amino-tris(hydroxymethyl)methane (Bis-tris) to ensure the safety and effectiveness of the monoclonal antibody. Thus, there is a need for methods of removing unwanted impurities from biologic compositions.

SUMMARY OF THE INVENTION

Many embodiments of the invention described herein relates to a method for purifying a biologic composition, comprising diafiltering the biologic composition with phosphate buffered saline (PBS) to obtain a purified composition.

In one embodiment, the biologic composition comprises at least one isolated protein.

In one embodiment, the isolated protein is a monoclonal antibody. In one embodiment, the monoclonal antibody is ch14.18.

In one embodiment, the biologic composition further comprises at least one impurity. In one embodiment, the impurity is bis(2-hydroxyethyl)amino-tris(hydroxymethyl)methane (Bis-tris). In one embodiment, the concentration of the Bis-tris in the biologic composition is 10 to 50 mM Bis-tris at a pH of 6.3 to 6.7.

In one embodiment, the diafiltering removes at least 50% of the Bis-tris from the biologic composition. In one embodiment, the diafiltering removes at least 70% of the Bis-tris from the biologic composition.

In one embodiment, the concentration of the PBS is 10 to 50 mM Sodium Phosphate and 100 to 200 mM NaCl.

In one embodiment, the monoclonal antibody is concentrated to a concentration of at least 2.0 to 5.0 AU before being diafiltered into the composition comprising PBS. In one embodiment, the monoclonal antibody is concentrated to a concentration of at least 4.0 to 6.0 AU before being diafiltered into the composition comprising PBS.

In one embodiment, the method further comprises isolating and purifying the monoclonal antibody using at least one chromatography column.

In one embodiment, the method comprises isolating and purifying the monoclonal antibody using at least one affinity chromatography column, at least one cation exchange chromatography column, and/or at least one anion exchange chromatography column. In one embodiment, the anion exchange chromatography column is a Capto™ adhere column. In one embodiment, the monoclonal antibody is eluted from the Capto™ adhere column using a composition comprising Bis-tris.

In one embodiment, at least three volume units of the biologic composition is diafiltered into one volume unit of the composition comprising PBS. In one embodiment, at least five volume units of the biologic composition is diafiltered into one volume unit of the composition comprising PBS.

In one embodiment, the purified composition is further diafiltered into a composition comprising histidine.

Further described is a method for purifying a monoclonal antibody, comprising:

(a) passing a first composition comprising the monoclonal antibody through an affinity chromatography column to obtain a second composition comprising the monoclonal antibody; (b) lowering the pH of the second composition to obtain a third composition; (c) washing the third composition with a solvent-detergent to obtained a fourth composition; (d) washing the fourth composition to remove the solvent-detergent to obtain a fifth composition; (e) passing the fifth composition through a cation exchange chromatography column to obtain a sixth composition comprising the monoclonal antibody; (f) subjecting the sixth composition to nano-filtration to obtain a seventh composition; (g) passing the seventh composition through an anion exchange chromatography column to obtain an eighth composition comprising the monoclonal antibody and Bis-tris; and (h) diafiltering the eighth composition into a composition comprising PBS to obtain a ninth composition comprising the monoclonal antibody but substantially free from Bis-tris.

DETAILED DESCRIPTION OF THE PREFERRED EMBODIMENTS

Figure 1:
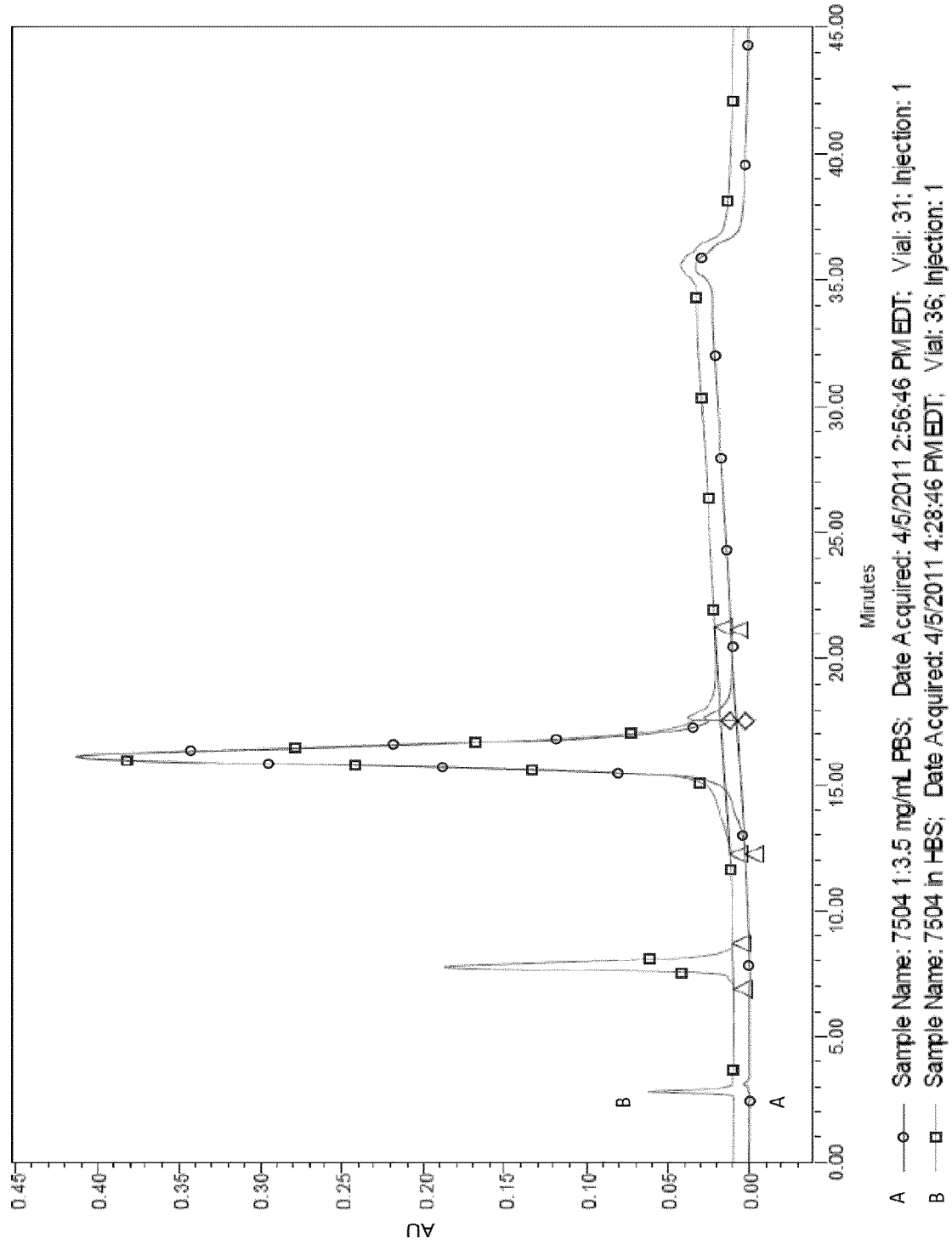
FIG. 1 shows weak cation exchange HPLC Analysis of ch14.18 after diafiltration with PBS. Line A represents ch14.18 diafiltered with PBS. Line B represents ch14.18 diafiltered into HBS, both monitored at 215 nm.

Many embodiments described herein relate to a method for purifying a biologic composition, comprising diafiltering the biologic composition with phosphate buffered saline (PBS), to obtain a purified composition.

Biologic Composition

Many biologic compositions known in the art can be purified using the methods described herein. The biologic composition can comprise at least one material created biologically rather than chemically synthesized, including proteins, nucleic acids, cells, tissues, vaccines, and blood or a component thereof.

The biologic composition can comprise, for example, at least one isolated protein including a recombinant protein. The biologic composition can comprise, for example, at least one isolated nucleic acid. The biologic composition can comprise, for example, at least one monoclonal antibody. The biologic composition can comprise, for example, at least one chimeric, altered, or humanized antibody.

In one particular embodiment, the biologic composition comprises at least one ch14.18 monoclonal antibody, although other antibodies and biologics can be purified by the teaching disclosed herein.

The biologic composition can comprise, for example, at least one impurity. The impurity can be, for example, an undesirable salt such as Bis-tris. The concentration of the Bis-tris impurity in the biologic composition can be, for example 1 to 100 mM Bis-tris, or 10 to 50 mM Bis-tris, or 20 to 40 mM Bis-tris. The pH can be, for example, 6 to 7, or 6.3 to 6.7, or 6.4 to 6.6.

Diafiltration with PBS

In some embodiments, the method described herein comprises diafiltering at least two, at least three, at least four, at least five, or at least six volume units of the biologic composition into one volume unit of PBS.

In some embodiments, the biologic composition comprises undesirable Bis-tris, and the method described herein comprises removing at least 30%, at least 50%, at least 70%, at least 90%, or at least 95% of the Bis-tris from the biologic composition by means of PBS diafiltration.

The concentration of the PBS can be, for example, 10 to 50 mM Sodium Phosphate, and 100 to 200 mM NaCl.

In some embodiments, prior to being diafiltered with PBS, the biologic composition is concentrated first.

In some embodiments, after the PBS diafiltration, the biological composition is diafiltered into a formulation comprising 20 mM histidine, 150 mM NaCl, and 0.05% Tween 20 saline (HBS).

Isolation of Monoclonal Antibody

In several embodiments described herein, the method also comprises isolating and purifying the monoclonal antibody before the PBS diafiltration. The monoclonal antibody can be isolated and purified by, for example, at least one chromatography column. The monoclonal antibody can be isolated and purified by, for example, at least one affinity chromatography column, at least one cation exchange chromatography column, and/or at least one anion exchange chromatography column. The anion exchange chromatography column can be, for example, a Capto™ adhere column.

Capto™ adhere column is known in the art and a commercially available from GE Healthcare Life Sciences. It is a multimodal medium for intermediate purification and polishing of monoclonal antibodies after capture on Protein A medium by packed bed chromatography. Some embodiments described herein comprises purifying a monoclonal antibody using Capto™ adhere column, wherein the monoclonal antibody is eluted with a composition comprising Bis-tris buffer. The eluted antibody formulation must then be diafiltered into a formulation comprising PBS, as discussed above, and optionally further diafiltered into a formulation comprising HBS.

The methods described herein can further comprise, for example, concentrating the biologic composition comprising harvested monoclonal antibody.

The methods described herein can further comprise, for example, diafiltering the biologic composition into Protein A equilibration buffer. In a particular aspect, the Protein A equilibration buffer comprises 25 to 100 mM Sodium Phosphate, 0.5 to 2.0 M NaCl, with pH 7.0 to 8.0.

The methods described herein can further comprise, for example, passing the biologic composition through an affinity chromatography column, such as a Protein A affinity column.

The methods described herein can further comprise, for example, viral inactivation by lowering the PH of the biologic composition.

The methods described herein can further comprise, for example, viral inactivation by washing the biologic composition with a solvent-detergent. In a particular aspect, the solvent-detergent comprises 10 to 25% Polysorbate (TWEEN), 5 to 10% Tributyl Phosphate.

The methods described herein can further comprise, for example, washing the biologic composition to remove any solvent-detergent.

The methods described herein can further comprise, for example, diafiltering the biologic composition into 50 HS equilibration buffer. In a particular aspect, the 50 HS equilibration buffer comprises 5 to 20 mM Citrate, 5 to 30 mM Phosphate, 15 to 100 mM Sodium Chloride, with pH 4.0 to 5.5.

The methods described herein can further comprise, for example, passing the biologic composition through a cation exchange affinity chromatography column such as a 50 HS column.

The methods described herein can further comprise, for example, subjecting the biologic composition to nano-filtration.

The methods described herein can further comprise, for example, passing the biologic composition through an anion exchange affinity chromatography column, such as a Capto™ adhere column before the PBS diafiltration. The monoclonal antibody can be eluted from the Capto™ adhere column using a Bis-tris buffer.

The methods described herein can further comprise, for example, diafiltering the biologic composition into a histidine buffer after the PBS diafiltration.

In one embodiment, the methods described herein comprises the following steps:
(a) passing a first composition comprising the monoclonal antibody through an affinity chromatography column to obtain a second composition comprising the monoclonal antibody;
(b) lowering the pH of the second composition to obtain a third composition;
(c) washing the third composition with a solvent-detergent to obtained a fourth composition;
(d) washing the fourth composition to remove the solvent-detergent to obtain a fifth composition;
(e) passing the fifth composition through a cation exchange chromatography column to obtain a sixth composition comprising the monoclonal antibody;
(f) subjecting the sixth composition to nano-filtration to obtain a seventh composition;
(g) passing the seventh composition through an anion exchange chromatography column to obtain an eighth composition comprising the monoclonal antibody and Bis-tris; and
(h) diafiltering the eighth composition into a composition comprising PBS to obtain a ninth composition comprising the monoclonal antibody but substantially free from Bis-tris.

WORKING EXAMPLES

Example 1—Development of Weak Cation Exchange HPLC Assay

Figure 5:
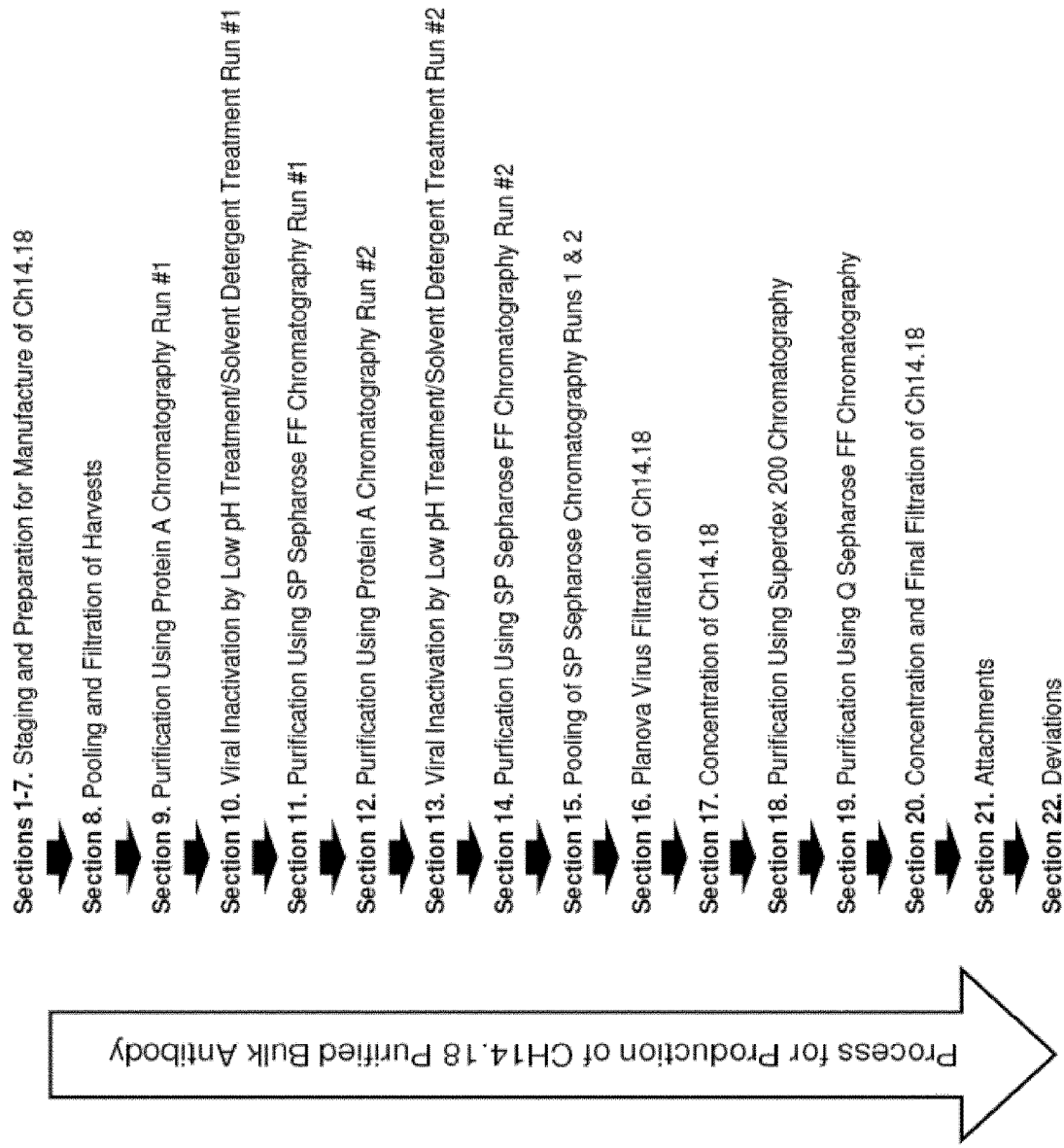
FIG. 5 provides a schematic depicting one embodiment of a process flow chart for purifying a monoclonal antibody (e.g., ch14.18). This purification process was initially developed by the National Cancer Institute (NCI) (see Example 2) and subsequently improved by United Therapeutics Corp (see Example 1).

In the development of the ch14.18 purification process, an objective was to improve the purification process which was initially developed by the National Cancer Institute (NCI) (see FIG. 5 for the process initially developed by the NCI). A further objective was to upgrade to chromatography resins which had better capacity, better flow properties, or were tolerant of harsher chemicals that could be useful to sanitize the resins prior to the next use (e.g., Capto™ adhere resin from GE Healthcare).

For the last two chromatography steps (see Sections 18 and 19 of FIG. 5), NCI used a Superdex 200 size-exclusion chromatography column to remove aggregates and dimers of ch14.18, followed by a Q Sepharose anion exchange resin as a polishing resin. They were upgraded to a resin that removes viruses, aggregates, and traces contaminants—the Capto™ adhere resin from GE Healthcare (see e.g., GE Healthcare Life Sciences, Instructions 28-9064-05 Capto™ adhere Affinity Chromatography product manual, which is incorporated herein by reference in its entirety and is available at gelifesciences.com/gehels_images/GELS/Related%20Content/Files/13346677 80708/litdoc28906405_20120420104439.pdf. This resin is a mixed mode resin, a combination of anion exchange and hydrophobic interaction. It was operated in the flow through mode, in which the contaminants bind to the resin, while the ch14.18 monoclonal antibody did not bind and remained in the flow-through.

At the same time that the purification of ch14.18 was being revised, quality indicating assays were also being developed. One of these was a weak cation exchange chromatography HPLC assay. For this, the TSKGEL CM-3SW column from TOSOH was used to assess the purity of ch14.18. For this analysis, the antibody bound to the column and eluted the column as a salt gradient was run through the column. The column was equilibrated in a low salt sodium phosphate buffer (buffer A) and the gradient was generated with an increased concentration of sodium phosphate/sodium perchlorate buffer (Buffer B). With this separation method the column effluent was monitored at 215 nm and the ch14.18 peak eluted from the column at approximately 15-19 minutes after injection. The retention time for ch14.18 varied as the method and gradient were being optimized. During the development of the assay, various samples of ch14.18 were tested and in some of them a fairly large peak, having a retention time of ~7.5 minutes was observed. In trying to identify this contaminant, samples of ch14.18 were spiked with contaminants that are added early in the manufacturing process (see FIG. 1). A sample of ch14.18 which did not contain the contaminant was spiked with methotrexate or tributyl phosphate and polysorbate 80. None of these contaminants appeared to be the source of the peak with the retention time of 7.5 minutes.

Figure 2:
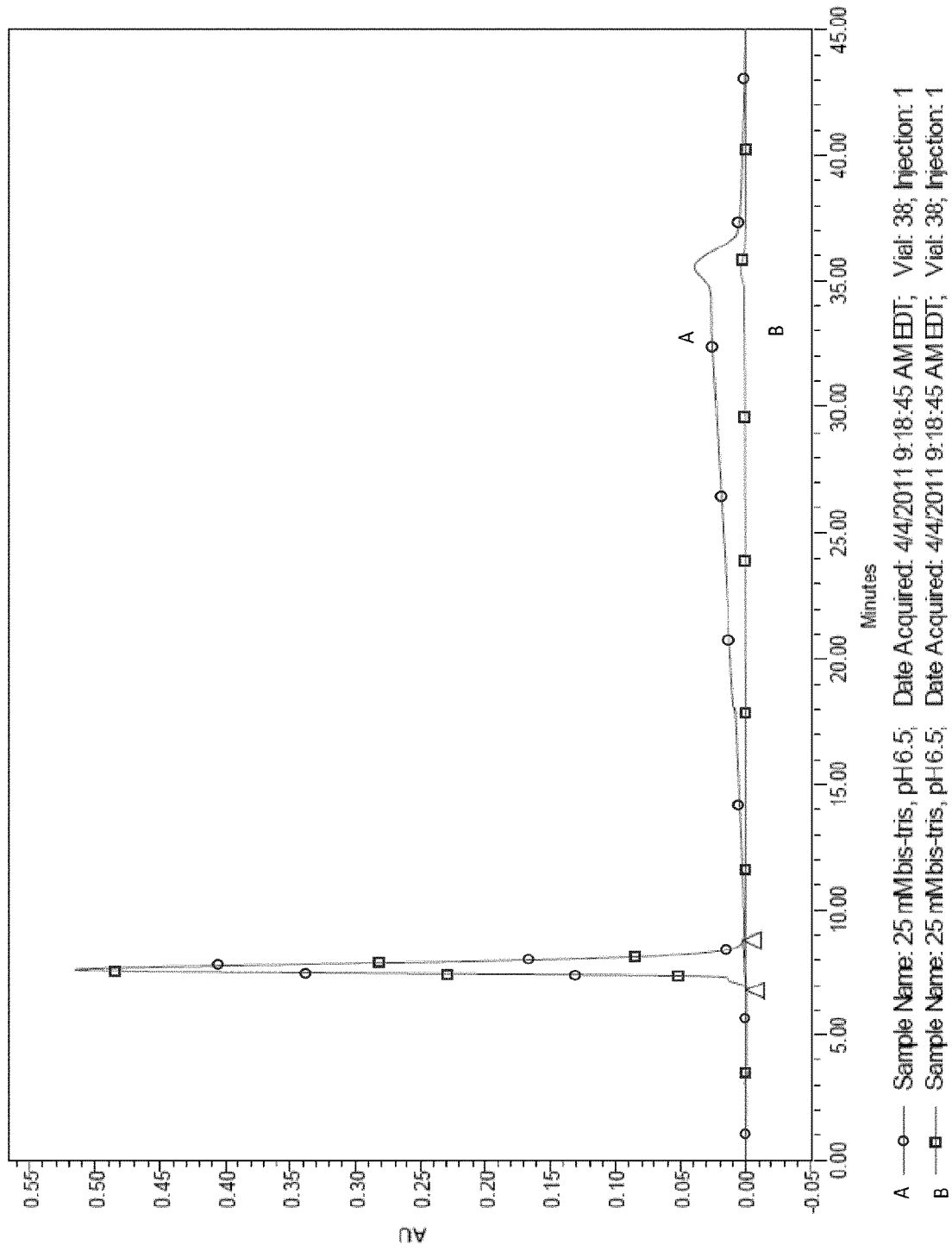
FIG. 2 shows sample of 25 mM Bis-tris loaded onto the weak cation exchange HPLC column, and demonstrates that the peak with a retention time of ~7 minutes is due to Bis-tris. Evaluation of 25 mM Bis-tris by weak cation exchange. Line A indicates the absorbance monitored at 215 nm. Line B indicates the absorbance monitored at 280 nm.

Through tracing the source of the samples and which step in the purification process the sample was derived from, it was noted that the peak at issue was only seen after Capto™ adhere chromatography, which was the final polishing step in the purification process. It was suspected that the contaminant was some trace contaminant, such as host cell protein from the cell culture process that was co-purifying and concentrating on the column. Samples from mock runs on a Capto™ adhere column which had been loaded on a used column or a new column were evaluated by weak cation exchange chromatography HPLC (see FIG. 2). The contaminant peak at 7.5 minutes was found in both samples at approximately the same concentration, indicating that the contaminant was not derived from upstream contaminants.

Figure 3:
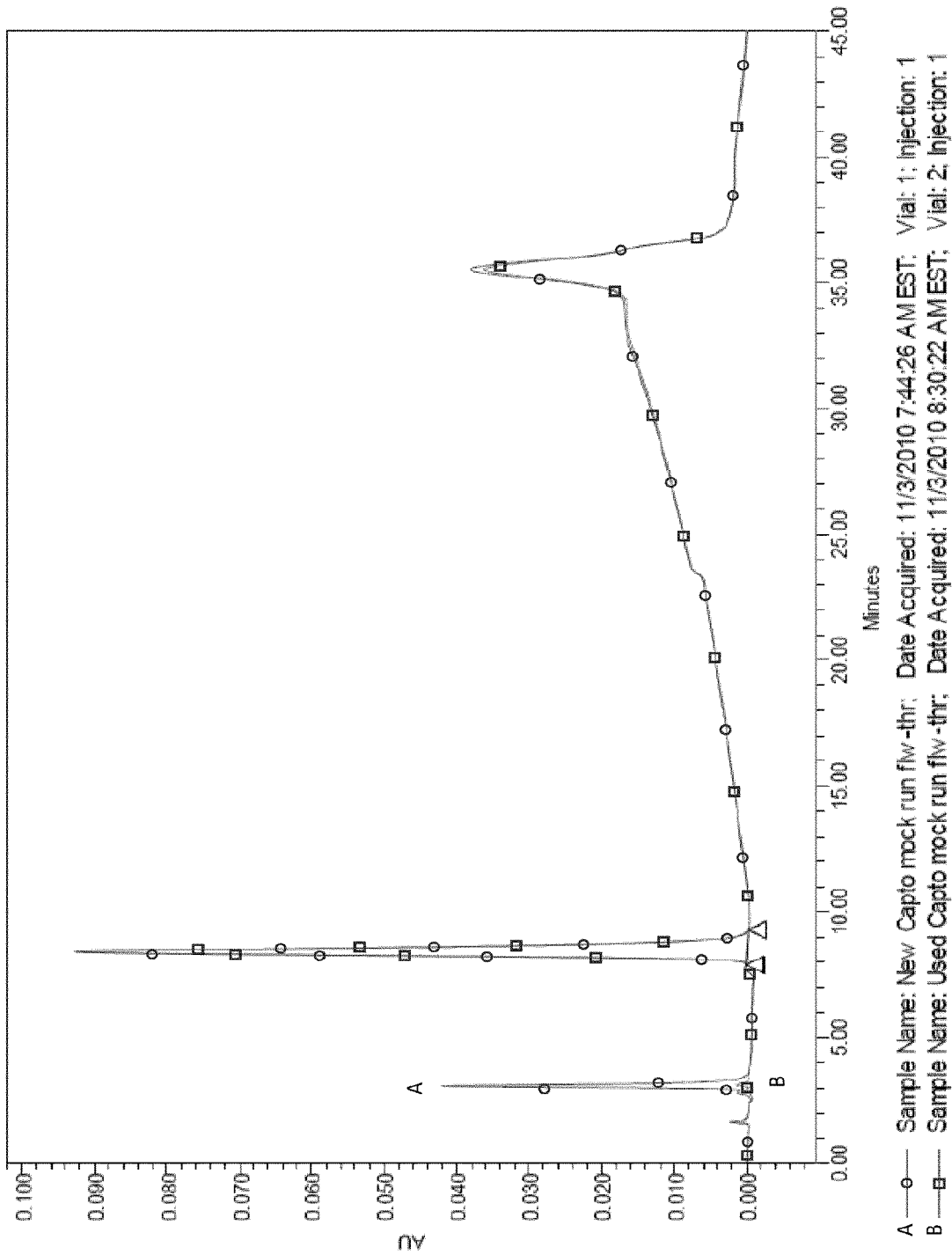
FIG. 3 shows weak cation HPLC of Capto™ adhere eluate pool from new or used resin, and demonstrates that the peak at ~7 minutes is due to Bis-tris and not to some contaminant on the column from prior usage. Samples of Capto™ adhere eluate pools, with no ch14.18 derived from new or used chromatography columns. Line A is for sample from the new column. Line B is from the used column.

By tracking the origin of the samples of ch14.18 which contained the samples and those that did not, it became apparent that the contaminant was Bis-tris which is the buffer salt used for the Capto™ adhere purification step (see FIG. 3).

Figure 4:
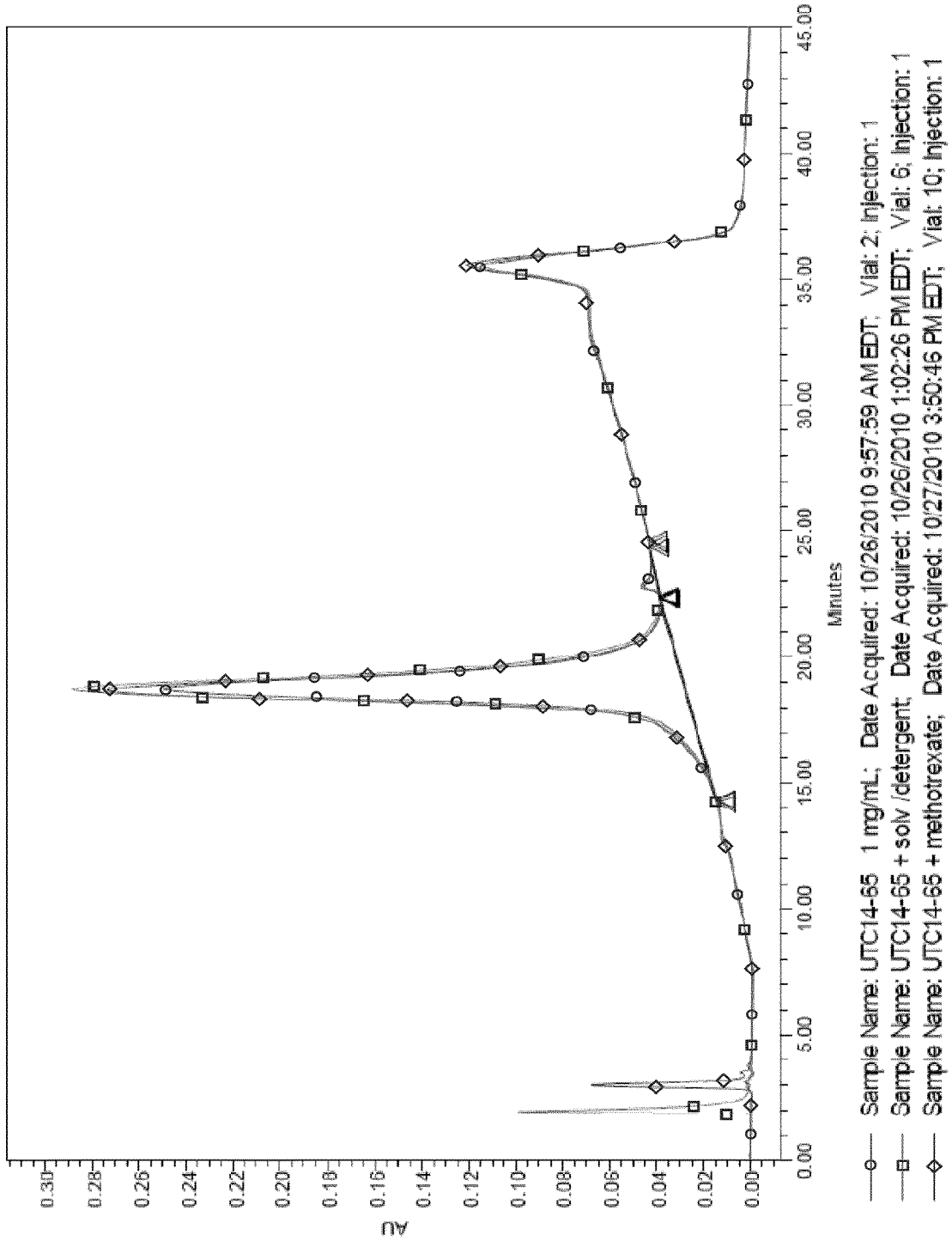
FIG. 4 shows weak cation exchange HPLC chromatography of ch14.18, spiked with contaminants prior to diafiltration into PBS. Line A represents ch14.18 with no contaminant spike. Line B represents ch14.18 spiked with tributyl phosphate and polysorbate 80. Line C represents ch14.18 spiked with methotrexate. None of the trace additives from the purification process are responsible for the peak at ~7 minutes (FIGS. 1 & 2).

Having identified the contaminant, investigated next was the reason that some of the purified ch14.18 samples, which had been through the entire purification process, contained the Bis-tris peak, whereas others did not. Also being developed is a final antibody formulation in 20 mM histidine, 150 mM NaCl, 0.05% Tween 20 saline (HBS), which was transitioned from a formulation in phosphate buffered saline (PBS) used by NCI. It was noted that if the Capto™ adhere product pool containing ch14.18 was diafiltered directly into the HBS buffer, the Bis-tris peak did not diafilter out of the retentate pool. However, if this pool was first diafiltered into phosphate buffered saline and then into the HBS buffer, the Bis-tris was completely removed from the solution. FIG. 4 shows ch14.18 from the Capto™ adhere chromatography step that had been diafiltered into HBS or diafiltered with PBS In conclusion, the Capto™ adhere column is commonly used in the biotechnology industry for the purification of monoclonal antibodies. It has utility for the removal of trace contaminants such as residual Protein A ligand, residual host cell DNA, residual host cell proteins, antibody aggregates, and viruses. Diafiltration with PBS was proved to be an effective way to remove the Bis-tris impurities prior to the final formulation of a monoclonal antibody such as ch14.18.

Example 2—Process Flow Chart

A Process Flow Chart is provided in FIG. 5 which depicts one embodiment for purifying a monoclonal antibody (e.g., Ch14.18). The process depicted is not meant to be strictly limited and may be adjusted in accordance with the particular needs and circumstances of the process at hand. The process of FIG. 5 generally refers to the following steps:

Section 8. Initial pooling and filtration of harvest of the monoclonal antibody (e.g., crude harvest).

Section 9. Passing the harvests of Section 8 through an affinity chromatography column (e.g., a Protein A chromatography column) to obtain a second composition comprising the monoclonal antibody.

Section 10. Inactivating viruses by lowering the pH of the second composition to obtain a third composition. The third composition is then washed with a solvent-detergent to obtained a fourth composition, which is then washed again to remove the solvent-detergent to obtain a fifth composition.

Section 11. Passing the fifth composition through a cation exchange chromatography column (e.g., SP Sepharose FF Chromatography) to obtain a sixth composition comprising the monoclonal antibody. The Protein A chromatography can be repeated (Section 12), followed by a repeating of the viral inactivation (Section 13), followed by a repeating of the cation exchange chromatography (e.g., Sepharose) (Section 14). The Sepharose runs are then pooled to form the sixth composition.

Section 16. Subjecting the sixth composition to nano-filtration to further remove viruses to obtain a seventh composition.

Sections 17, 18, 19. Concentrating the monoclonal antibody by passing the seventh composition through a Superdex 200 size-exclusion chromatography column to remove aggregates and dimers of the monoclonal antibody. The composition is then passed through a Q Sepharose anion exchange resin to obtain an eighth composition comprising the monoclonal antibody.

Section 20. Concentration and Final Filtration. The eighth composition is then subjected to concentration and final filtration, including diafiltration into a composition comprising PBS, to obtain a ninth composition comprising the monoclonal antibody.

Additional Embodiments

Embodiment 1—A method for purifying a biologic composition, comprising diafiltering the biologic composition with phosphate buffered saline (PBS) to obtain a purified composition.

Embodiment 2—The method of embodiment 1, wherein the biologic composition comprises at least one isolated protein.

Embodiment 3—The method of any of embodiments 1 to 2, wherein the biologic composition comprises at least one isolated monoclonal antibody such as ch14.18.

Embodiment 4—The method of any of embodiments 1 to 3, wherein the biologic composition further comprises at least one impurity such as bis(2-hydroxyethyl)amino-tris(hydroxymethyl)methane (Bis-tris).

Embodiment 5—The method of any of embodiments 1 to 4, wherein the biologic composition further comprises Bis-tris at a concentration of 10 to 50 mM Bis-tris at a pH of 6.3 to 6.7.

Embodiment 6—The method of any of embodiments 1 to 5, wherein the diafiltering removes at least 50%, at least 70%, or at least 90% of the Bis-tris from the biologic composition.

Embodiment 7—The method of any of embodiments 1 to 6, wherein the concentration of the PBS is 10 to 50 mM Sodium Phosphate and 100 to 200 mM NaCl.

Embodiment 8—The method of any of embodiments 1 to 7, wherein the monoclonal antibody is concentrated to a concentration of at least 2.0 to 5.0 AU, before being diafiltered into the composition comprising PBS.

Embodiment 9—The method of any of embodiments 1 to 8, comprising isolating and purifying the monoclonal antibody using at least one chromatography column.

Embodiment 10—The method of any of embodiments 1 to 9, comprising isolating and purifying the monoclonal antibody using at least one affinity chromatography column, at least one cation exchange chromatography column, and/or at least one anion exchange chromatography column such as Capto™ adhere column.

Embodiment 11—The method of any of embodiments 1 to 10, wherein the monoclonal antibody is eluted from the Capto™ adhere column using a composition comprising Bis-tris before being diafiltered with PBS.

Embodiment 12—The method of any of embodiments 1 to 11, wherein at least three volume units, least four volume units, least five volume units, or least six volume units of the biologic composition is diafiltered into one volume unit of the composition comprising PBS.

Embodiment 13—The method of any of embodiments 1 to 12, wherein the purified composition is further diafiltered into a composition comprising histidine.

Embodiment 14—A method for purifying a monoclonal antibody, comprising: (a) passing a first composition comprising the monoclonal antibody through an affinity chromatography column to obtain a second composition comprising the monoclonal antibody; (b) lowering the pH of the second composition to obtain a third composition; (c) washing the third composition with a solvent-detergent to obtained a fourth composition; (d) washing the fourth composition to remove the solvent-detergent to obtain a fifth composition; (e) passing the fifth composition through a cation exchange chromatography column to obtain a sixth composition comprising the monoclonal antibody; (f) subjecting the sixth composition to nano-filtration to obtain a seventh composition; (g) passing the seventh composition through an anion exchange chromatography column to obtain an eighth composition comprising the monoclonal antibody and Bis-tris; and (h) diafiltering the eighth composition into a composition comprising PBS to obtain a ninth composition comprising the monoclonal antibody but substantially free from Bis-tris.

What is claimed is:

1. A method for purifying a biologic composition, comprising diafiltering the biologic composition with phosphate buffered saline (PBS) to obtain a purified composition, wherein the biologic composition prior to purification comprises bis(2-hydroxyethyl) amino-tris(hydroxymethyl)methane (Bis-tris), wherein the diafiltering removes at least 50% of the Bis-tris from the biologic composition, wherein the concentration of the PBS is 10 to 50 mM Sodium Phosphate and 100 to 200 mM NaCl, and wherein the biological composition does not comprise a ch14.18 antibody.

2. The method of claim 1, wherein the biologic composition comprises at least one isolated protein.

3. The method of claim 2, wherein the isolated protein is a monoclonal antibody.

4. The method of claim 1, wherein the concentration of the Bis-tris in the biologic composition is 10 to 50 mM Bis-tris at a pH of 6.3 to 6.7.

5. The method of claim 1, wherein the diafiltering removes at least 70% of the Bis-tris from the biologic composition.

6. The method of claim 3, further comprising isolating and purifying the monoclonal antibody using at least one chromatography column.

7. The method of claim 3, comprising isolating and purifying the monoclonal antibody using at least one affinity chromatography column, at least one cation exchange chromatography column, and/or at least one anion exchange chromatography column.

8. The method of claim 7, wherein the anion exchange chromatography column is a multimodal medium column.

9. The method of claim 8, wherein the monoclonal antibody is eluted from the multimodal medium column using a composition comprising Bis-tris.

10. The method of claim 1, wherein at least three volume units of the biologic composition is diafiltered into one volume unit of the composition comprising PBS.

11. The method of claim 1, wherein at least five volume units of the biologic composition is diafiltered into one volume unit of the composition comprising PBS.

12. The method of claim 1, wherein the purified composition is further diafiltered into a composition comprising histidine.

\* \* \* \* \*